United States Patent [19]
Albrecht et al.

[11] Patent Number: 4,979,110
[45] Date of Patent: Dec. 18, 1990

[54] CHARACTERIZING THE STATISTICAL PROPERTIES OF A BIOLOGICAL SIGNAL

[75] Inventors: Paul Albrecht, Weston; Richard J. Cohen, Waban, both of Mass.

[73] Assignee: Massachusetts Institute of Technology, Cambridge, Mass.

[21] Appl. No.: 247,738

[22] Filed: Sep. 22, 1988

[51] Int. Cl.$^5$ .............................................. G06F 15/42
[52] U.S. Cl. ......................... 364/413.03; 364/413.05; 364/413.06; 364/728.07; 128/670; 128/700; 128/702
[58] Field of Search ...................... 364/413.03, 413.05, 364/413.06.728.07; 18/670, 671, 672, 700, 702

[56] References Cited

PUBLICATIONS

Parzen, Sankhya A., vol. 25 (1963), on Spectral Analysis with Missing Observations and Amplitude Modulation.
Bloomfield, J. R., Statis, Soc. B (1970), Special Analysis with Randomly Missing Observations.
Scheinok, Ann. Math. Statis., vol. 36 (1965), Spectral Analysis with Randomly Missed Observations: the Binomial Case.
Pagani et al., Cir. Res., vol 59 (1986), Power Spectral Analysis of Heart Rate and Arterial Pressure Variabilities as a Marker of Sympatho Vagal Interaction in Man and Conscious Dog.
Akselrod et al., Science, vol. 213 (1981), Power Spectrum Analysis of Heart Rate Fluctuation: a Quantitative Probe of Beat-To-Beat Cardiovascular Control.
Pomeranz et al., M. J., Phys. vol. 248 (1985), Assessment of Autonomic Function in Humans by Heart Rate Spectral Analysis.
Berger et al., IEEE Trans. Biomed. Eng., vol. BME-33 (1986), An Efficient Algorithm for Spectral Analysis of Heart Rate Variability.
Van Der Akker et al. Automedica, vol. 4 (1983), Heart Rate Variability and Blood Pressure Oscillations in Diabetics with Autonomic Neuropathy.
Saul et al., Am. J. Cardiol., vol. 61 (1988), Assessment of Autonomic Regulation in Chronic Congestive Heart Failure by Heart Rate Spectral Analysis.
Myers, et al., IEEE Trans. on Biomedical Eng., vol. BME-33 (1986), Power Spectral Analysis of Heart Rate Variability in Sudden Cardiac Death: Comparison to Other Methods.

*Primary Examiner*—Jerry Smith
*Assistant Examiner*—Steven G. Kibby
*Attorney, Agent, or Firm*—Choate, Hall & Stewart

[57] ABSTRACT

The statistical properties of a biological signal intermittently obscured by a relatively independent biological process are estimated by noting the time intervals during which the obscuring process is occurring. From the time intervals, a windowing function is constructed which makes a transition from one towards zero as the process obscures the signal and a transition towards one as the process terminates. Thereafter, a statistical characterization is performed in which the windowing function is used to weight the relative contributions of corresponding segments of the biological signal. In preferred embodiments, the statistical properties include the autocorrelation function and power spectrum of biological signals such as heart rate and blood pressure. The invention is applicable also to estimating the cross-correlation and transfer function of a first signal intermittently obscured by a first process and a second signal intermittently obscured by a second process in which each of the signals are relatively independent of each of the obscuring processes. When the biological signal is heart rate, the obscuring process may be the occurrence of ectopic beats. Intervals which contain ectopic beats are treated as though they are missing. In this way, data which might otherwise be unusable by virtue of ectopic beats can become useful for assessing the status of the biological system.

19 Claims, 2 Drawing Sheets

CHARACTERIZING THE STATISTICAL PROPERTIES OF A BIOLOGICAL SIGNAL

BACKGROUND OF THE INVENTION

The role of the cardiovascular system is to provide an adequate supply of oxygenated blood to the tissues and organs of the body. This function is carefully regulated by the autonomic nervous system (ANS), which continuously senses systemic blood pressure and other hemodynamic variables that reflect the adequacy of tissue perfusion. The input sensed by the ANS is processed by the brain stem, which compares the inputs to desired set points. If the inputs deviate from the set points, the ANS is activated and attempts correct for the difference by bringing about changes in heart rate and vascular tone. This constant feedback and correction by the ANS is reflected in the fluctuations in heart rate (HR) and blood pressure (BP).

Measurements of HR and BP have long been used to characterize an individual's overall cardiovascular health. The measurements have typically consisted of mean values of the HR and BP made at a few points in time; the fluctuations in HR and BP have usually been disregarded. More recently, however, the value and relevance of studying the fluctuations in HR and BP has been demonstrated [1-7]. (Numbers in brackets refer to the references listed at the end of this specification, the teachings of which are incorporated herein by reference.) It has been shown that fluctuations in HR and BP (as measured by their power spectra) and their joint fluctuation (as measured by transfer functions) can provide insight into the level of ANS activity and the physiologic state of the cardiovascular system. This finding has motivated the development of methodologies for using power spectrum and transfer function analysis as a noninvasive physiologic probe [1-7].

An important application for such a methodology is in the evaluation of an older and sicker patient population. Such a population is very likely to have ectopic beats—beats which originate in parts of the heart other than the sinoatrial node (SAN). Whereas the timing of the beats which originate in the SAN is directly modulated by the ANS, the timing and occurrence of ectopic beats is not considered an indicator of cardiovascular feedback and control. From the perspective of power spectrum and transfer function analysis, ectopic beats are a contaminating signal which overshadows the normal activity of the SAN.

The current state of the art is to deal with ectopic beats in one of two ways. One approach is to wait for a sufficiently long interval which is free of ectopic beats [5, 6]. While this method is effective in a younger and healthier population, it is often impractical, if not impossible, in an older and sicker clinical population which has more frequent ectopic beats. The second approach is to estimate what the HR and BP would have been if they had not been obscured by the ectopic beats, and then to substitute those HR and BP estimates in intervals containing ectopic beats. It is common practice to replace the HR and BP by a simple linear spline or weighted average of the points bordering the ectopic beat intervals [4, 7]. However, such simple estimates make unwarranted assumptions about the HR and BP, especially if the ectopic intervals last more than a few seconds.

SUMMARY OF THE INVENTION

The method according to one aspect of the invention for characterizing the statistical properties of a biological signal intermittently obscured by a relatively independent biological process includes noting the time intervals during which the obscuring process is occurring. A windowing function is constructed from the intervals. This windowing function makes a transition from one toward zero as the process obscures the signal and a transition towards one as the process terminates. The windowing function is used to weight the relative contributions of corresponding segments of the biological signal so that a statistical characterization of the signal can be performed. In one embodiment, the statistical property is the autocorrelation function of a biological signal and the product of the windowing function and the signal is taken. Both the autocorrelation of the product and the autocorrelation of the windowing function are computed. Thereafter, the quotient of the autocorrelation of the product by the autocorrelation of the windowing function is computed to estimate the autocorrelation function of the biological signal. If the power spectrum of the biological signal is desired, it may be computed from the quotient computed above.

In another aspect of the invention, the crosscorrelation function of a first signal intermittently obscured by a first process and a second signal intermittently obscured by a second process (which may or may not be the same as the first obscuring process) is computed. In this case, each of the signals is relatively independent of each of the obscuring processes. This method notes the time intervals during which the first obscuring process occurs. From these time intervals, a first windowing function is constructed which makes a transition from one towards zero as the first process obscures the first signal and a transition towards one as the first process terminates. The time intervals during which the second obscuring process is occurring is also noted and a second windowing function is constructed from the second set of time intervals. The second windowing function makes a transition from one toward zero as the second process obscures the second signal and a transition towards one as the second process terminates. The product of the first signal with the first windowing function and the product of the second signal with the second windowing function are computed. The crosscorrelation of the two products and the crosscorrelation of the two windowing functions are then computed followed by computing the quotient of the crosscorrelation of the products by the crosscorrelation of the windowing functions. The cross-spectrum of the two signals may be computed from the crosscorrelation function by computing the cross-spectrum from the crosscorrelation function.

The transfer function between the two signals may also be obtained by computing the cross-spectrum as set forth above and computing the power spectrum of the first of the two signals, also as set forth above, and then computing the quotient of the cross-spectrum and the power spectrum. The impulse response function between two signals is computed by taking the inverse Fourier transform of the transfer function. The impulse response function can also be computed directly from the crosscorrelation and autocorrelation functions which are computed as set out above. Similarly, the transfer function between two signals may be computed directly from the crosscorrelation function and the autocorrelation function. Alternatively, the transfer function between two signals is determined by computing the impulse response function and taking its Fourier transform.

The present invention characterizes statistical properties of a biological signal intermittently obscured by a relatively independent biological process. For example, power spectra and transfer functions of heart rate signals can be estimated for data containing ectopic beats. Instead of trying to "guess" what the obscured heart rate or other signal would have been, the method of the invention treats the heart rate signal during ectopic intervals as "missing data." The computation of the power spectra and transfer functions is based on auto- and crosscorrelation functions which make no direct reference to the heart rate or other signal during the ectopic intervals. The method of the present invention is fundamentally different from all existing strategies because it does not attempt to make explicit assumptions about the biological signal during the ectopic interval. The method does, however, assume that the autonomic nervous system activity is not substantially affected by the ectopic beats, and that the biological signal trends on either side of the missing data are part of an ongoing response.

By treating the ectopic intervals as "missing data", the method takes advantage of signal processing strategies which have been developed for dealing with signals that are only partially available. Previously, such strategies have been used for dealing with the problem of a receiving or recording device which has failed to faithfully receive or reconstruct a signal [8, 9]. In the biological context of the present invention, there is no difficulty in acquiring the signal. Relabelling the ectopic intervals as "missing data" permits the biological problem to be recast in a way which takes advantage of existing signal processing strategies. Computations on experimental data confirm that estimates computed according to the present invention give better results than prior art techniques involving splining.

BRIEF DESCRIPTION OF THE DRAWING

FIG. 1a is a graph of a function m(t) which represents the level of combined influences modulating the sinoatrial node;

FIG. 1b is a graph of the ECG corresponding to the function in FIG. 1a;

FIG. 1c is the instantaneous heart rate tachometer signal estimated from the ECG of FIG. 1b;

FIG. 1d is a graph of the estimate of heart rate;

FIG. 1e is a graph of a windowing function;

DESCRIPTION OF THE PREFERRED EMBODIMENT

Figure 1:
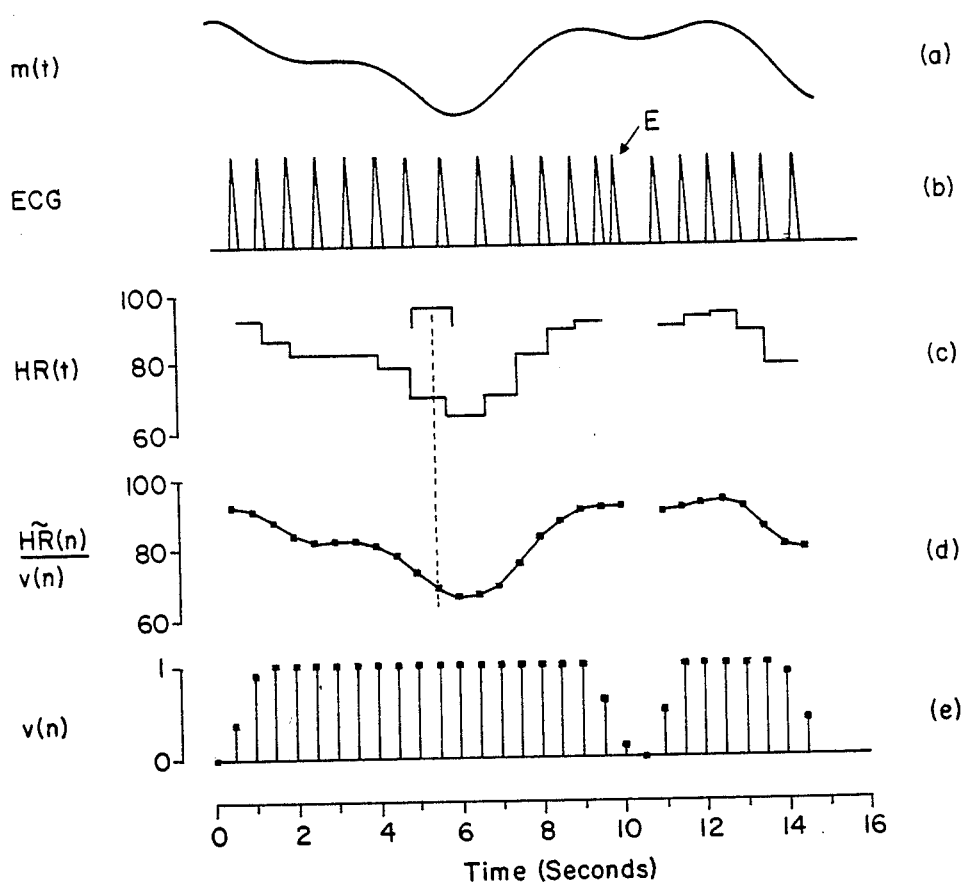

First of all, the theory on which the present invention is based will now be presented.

Assume that one would like to know the power spectra and transfer function of two biological signals x[n] and y[n] (e.g., HR and BP), but that we do not have full information on x[n] and y[n]. The versions of x[n] and y[n] available to us are intermittently obscured by some interfering process (e.g., ectopic beats). The series v[n] indicates the parts of x[n] that were obscured, and w[n] indicates the parts of y[n] that were obscured. All four time series are assumed to be time aligned and that each one consists of N samples taken at intervals of $T_s$ seconds. In specific:

x[n] is the time series that we would have observed if parts of the first signal had not been obscured.

y[n] is the time series that we would have observed if parts of the second signal had not been obscured.

v[n] is a time series which is defined to be 0 during times in which x[n] was obscured and 1 otherwise. It is assumed that v[n] is independent of x[n] and y[n].

w[n] is a time series which is defined to be 0 during times in which y[n] was obscured and 1 otherwise. It is assumed that w[n] is independent of x[n] and y[n].

$\tilde{x}[n]$ is defined as $\tilde{x}[n] = v[n]x[n]$.

$\tilde{y}[n]$ is defined as $\tilde{y}[n] = w[n]y[n]$.

The conventional estimate of the autocorrelation of x[n] in the absence of an obscuring signal is $$\hat{R}_x[k] = \frac{1}{N-k} \sum_{n=0}^{N-|k|-1} x[n]x[n+k]. \tag{1}$$

With the addition of an obscuring signal we introduce the modified autocorrelation estimate $$\hat{R}_{\tilde{x}}[k] = \frac{1}{N_k} \sum_n \tilde{x}[n]\tilde{x}[n+k], \tag{2}$$

where $N_k$ is defined as the number of $\tilde{x}[n]\tilde{x}[n+k]$ terms for which $v[n] = v[n+k] = 1$, and where the restricted sum is taken only over those $N_k$ terms. When no data is missing equations (1) and (2) are equivalent.

Equation (2) is a special case of a more general formula involving the autocorrelations $R_{\tilde{x}}[k]$ and $R_v[k]$. It can be shown that if $\tilde{x}[n] = v[n]x[n]$, where $\tilde{x}[n]$ and v[n] are independent, and if $R_v[k] \neq 0$, then $$\hat{R}_x[k] = \frac{\hat{R}_{\tilde{x}}[k]}{R_v[k]}. \tag{3a}$$

is an asymptotically unbiased estimate of $R_x[k]$ [10]. By direct analogy, the autocorrelation estimate for y is $$\hat{R}_y[k] = \frac{\hat{R}_{\tilde{y}}[k]}{R_w[k]}. \tag{3b}$$

In addition, we introduce the relationship for the crosscorrelation estimate given by $$\hat{R}_{xy}[k] = \frac{\hat{R}_{\tilde{x}\tilde{y}}[k]}{R_{vw}[k]}, \tag{3c}$$

where $$\hat{R}_{\tilde{x}\tilde{y}}[k] = \frac{1}{N_k} \sum_n \tilde{x}[n]\tilde{y}[n+k], \tag{4a}$$

and is analogous to equation (2), and $$\hat{R}_{vw}[k] = \frac{1}{N-k} \sum_{n=1}^{N-|k|-1} v[n]w[n+k]. \qquad (4b)$$

It should be noted that, although in the definitions given above, v[n] and w[n] are defined to be 0 or 1, this condition is not a necessary restriction. Equations (3a–c) are valid even if v[n] and w[n] take on intermediate values between 0 and 1. If the definition of the problem at hand is such that use of intermediate values makes sense, then they can be used. That is, the windowing functions v[n] and w[n] make a transition from one toward zero as the process obscures the signal and a transition towards one as the process terminates.

Next, computation of the correlation estimates will be discussed. We start with the values x̃[n], ỹ[n], v[n], and w[n] for n=1, ... N. The first step is to de-trend x̃[n] and ỹ[n]. Although this biases the estimated correlations, the bias is minor and affects mostly the very low frequency region of the spectrum. Failure to remove large low frequency trends can subsequently cause a substantial increase in the variance of the entire spectrum or transfer function. When possible, it is best to compute the trend for x[n] using only values of x̃[n] for which v[n]=1. Once the trend is computed x̃[n] is adjusted by subtracting from it the product of v[n] and the trend at sample n. A similar detrending is carried out with ỹ[n] and w[n].

We then use FFT-based convolution to compute $(N-k)\hat{R}_x[k]$, $(N-k)\hat{R}_y[k]$, $(N-k)\hat{R}_{xy}[k]$, $(N-k)\hat{R}_v[k]$, $(N-k)\hat{R}_w[k]$, and $(N-k)\hat{R}_{vw}[k]$. From these we compute $\hat{R}_x[k]$, $\hat{R}_y[k]$, and $\hat{R}_{xy}[k]$ according to equations (3a–c). Values of k for which $\hat{R}[k] \cong 0$, where $\hat{R}[k]$ can be either $\hat{R}_v[k]$, $\hat{R}_w[k]$, or $\hat{R}_{vw}[k]$, we set $\hat{R}[k]=\hat{R}[k-1]$. This kind of singular condition rarely occurs except for large values of k, and is usually of little consequence in the estimation.

With the autocorrelation and crosscorrelation estimates in hand, one can then estimate the spectra $\hat{S}_x(f)$, $\hat{S}_y(f)$, and transfer function $\hat{H}_{xy}(f)$. These estimates can be made using parametric or FFT-based techniques [11, 12]. Using FFT-based techniques, the relevant power spectra and transfer function estimates are:

$$\hat{S}_x(f) = T_s DTFT(q[k]\hat{R}_x[k]) \quad x \text{ Power Spectrum,} \qquad (5a)$$

$$\hat{S}_y(f) = T_s DTFT(q[k]\hat{R}_y[k]) \quad y \text{ Power Spectrum, and} \qquad (5b)$$

$$\hat{H}_{xy}(f) = \frac{DTFT(q[k]\hat{R}_{xy}[k])}{DTFT(q[k]\hat{R}_x[k])} \quad x \text{ to } y \text{ Transfer Function,} \qquad (5c)$$

where DTFT stands for the Discrete Time Fourier Transform and q[k] is a windowing function chosen to achieve a desired level of spectral smoothing. The coherence $\hat{K}(f)$ and impulse response $\hat{h}(t)$ are then estimated as $$\hat{K}(f) = \frac{|\hat{S}_{xy}(f)|^2}{\hat{S}_x(f)\hat{S}_y(f)} \quad \text{coherence,} \qquad (5d)$$

$$\hat{h}(t) = DTFT^{-1}(Q(f)\hat{H}_{xy}(F)) \quad \text{impulse response,} \qquad (5e)$$

where Q(f) is a low-pass filter chosen to eliminate the high frequency portion of $\hat{H}_{xy}(f)$ beyond which $\hat{K}(f)$ is substantially decreased.

Parametric techniques like autoregressive (AR) or autoregressive moving average (ARMA) models can compute the spectra, transfer function, and impulse response directly from the auto- and crosscorrelation without the use of the FFT. Parametric techniques have the advantage of weighting the major spectral features more heavily and hence usually require fewer degrees of freedom to specify the result. In addition, parametric transfer functions estimates can be forced to yield a causal relationship between the input and output. FFT-based methods, on the other hand, require more degrees of freedom to represent the result, but weight all parts of the spectrum equally.

We present the estimation of the HR power spectrum as an example of the method described above. We assume that we have already processed the ECG data, and that we have at our disposal an annotation stream consisting of beat types (normal or ectopic) and times-of-occurrence. Such a stream of annotations is typical of what would be produced by many present-day clinical ECG analysis instruments. In the case of HR, the obscuring events are the ectopic beats.

Below, we first describe the method by which we would generate the time series HR[n] and v[n]. Afterwards we give an example of how a spectral estimate derived using the new method compares to the estimate derived from a conventional strategy which uses splining to fill in the ectopic intervals.

We have previously reported [13] a computationally efficient algorithm which takes as its input $\{t_i\}$, the times-of-occurrence of the beats, and produces H̃R[n], a discrete instantaneous HR estimate at a sampling frequency $f_s = 1/T_s$. The algorithm is based on the integral pulse frequency model (IPFM) of SAN modulation. In the model, the influence of the ANS is represented by a modulating function m(t) which is the rate at which the SAN approaches the next beat firing.

The IPFM model is appropriate since integration of the modulation function m(t) is analogous to the charging of the phase 4 transmembrane potential of the SAN cells. For the simple model with no lockout after firing, m(t) is proportional to the instantaneous heart rate. It has been shown that for the IPFM model, H̃R[n] yields a better spectral estimate for m(t) (i.e., lower harmonic and intermodulation distortion) than estimates based on other time series [13].

We have extended our algorithm to handle ectopic beats (see FIG. 1). In FIG. 1a the function m(t) represents the level of the combined influences modulating the SAN. The SAN integrates m(t). When the integral reaches a threshold, a beat is produced and the SAN begins integrating again. The goal of HR spectral estimation is to recover the spectrum of m(t). FIG. 1b is the ECG corresponding to m(t) from FIG. 1a. Each triangle in FIG. 1b represents one beat. The beat labelled E is an artificially introduced ectopic beat which did not originate in the SAN; E can be considered an atrial or ventricular ectopic beat. In FIG. 1c, the function HR(t) is the instantaneous HR tachometer estimated from the RR intervals of the ECG. Note that the value of HR(t) for two intervals bounded by the ectopic beat is unknown. FIG. 1d is the estimate of H̃R[n] given by HR[n]/v[n] and FIG. 1e is the windowing function v[n]. Both H̃R[n] and v[n] were calculated using $T_s = 0.5$, which corresponds to a sampling frequency of $f_s = 2$Hz. Note that FIG. 1c at 5.5 seconds shows a rectangular window used in deriving the corresponding point in FIG. 1d. At zero and 10.5 seconds such an estimate was not possible since v[n]=0.

As before, we first compute $RR_i = t_{i+1} - t_i$ for the ith interval, and estimate the instantaneous HR tachometer as $$HR(t) = \frac{60}{RR_i}, \quad t = [t_i, t_{i+1}). \quad (6)$$

We then compute discrete samples from the low-pass (anti-alias) filtered tachometer but, instead of computing $$\hat{HR}[n] = \frac{1}{2T_s} \int_{(n-1)T_s}^{(n+1)T_s} HR(t)dt, \quad (7)$$

as we do in the case of no ectopic intervals, we compute $$\hat{HR}[n] = \frac{1}{2T_s} \int_{(n-1)T_s}^{(n+1)T_s} v(t)HR(t)dt, \quad (8)$$

where v(t) is a windowing function defined by $$v(t) = \begin{cases} 0 & \text{if } t \text{ falls in a ectopic interval} \\ 1 & \text{if } HR(t) \text{ is known} \end{cases} \quad (9)$$

Equations (6) and (7) represent samples of waveforms which have been convolved with a rectangular filter of width $2T_s$, and sampled at times $nT_s$. When there are no ectopic intervals, $\hat{HR}[n] = HR[n]$.

Observing that HR(t) is piece-wise constant, we can write equation (7) as $$\hat{HR}[n] = \sum_i \frac{60 \, \Delta t_i}{RR_i \, 2T_s}, \quad (10)$$

where $\Delta t_i$ is the part of $RR_i$ contained in the interval $[(n-1)T_s, (n+1)T_s]$. For example, if 20% of $RR_i$ is in the interval, then $\Delta t_i = 0.2 RR_i$. If $RR_i$ is an ectopic interval, we set $\Delta t_i = 0$. Defining v[n] as $$v[n] = \sum_i \frac{\Delta t_i}{2T_s} = \frac{1}{2T_s} \int_{(n-1)T_s}^{(n+1)T_s} v(t)dt, \quad (11)$$

we can approximate HR[n] as $$HR[n] \approx v[n]HR[n]. \quad (12)$$

For output series with $T_s$ shorter than the mean RR interval, we often extend the duration of the ectopic interval to the next multiple of $T_s$. This modification is accomplished by setting $v[n] = HR[n] = 0$ for $v[n] < 1$, and has the advantage of turning equation (12) into an equality. The disadvantage is that a smaller fraction of the available HR(t) is used for estimation; however, when $T_s$ is shorter than the mean RR interval, the additional data declared "missing" is usually small.

It should be noted that the rectangular filter implicit in equation (7) multiplies the spectrum of HR(t) by $$F(f) = \left( \frac{\sin(2\pi f/f_s)}{2\pi f/f_s} \right)^2. \quad (13)$$

hence any spectrum computed using HR[n] and v[n] must be compensated by dividing with F(f). Furthermore, since the F(f) approaches zero at $f_s/2$, the HR spectrum cannot be considered valid much beyond $f_s/4$.

Figure 2A:
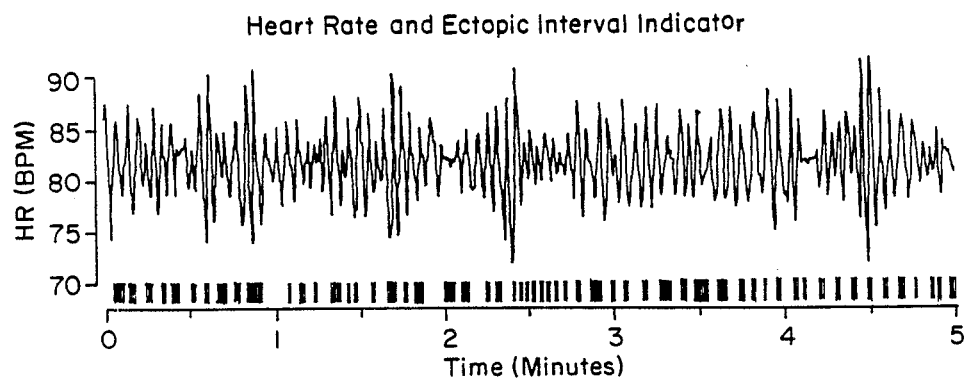
FIG. 2a is a graph of a simulated heart rate signal including a bar code representing ectopic intervals.

FIG. 2 compares a spectrum computed according to the method of the invention (labelled "New" in the Figure) to a spectrum computed from a HR[n] series filled in by splining. FIG. 2a is a five minute simulated HR[n] signal sampled at $T_s = 0.5$ seconds. The signal has the spectral content typical of the high frequency, respiration-induced component of HR. Immediately under HR[n] is a bar code which represents the ectopic intervals. The dark part of the bar indicates the "missing data", and accounts for 45% of the 5 minutes. The ectopic interval pattern is not simulated, but is taken from an actual clinical ECG containing substantial ectopy.

Figures 2B, 2C:
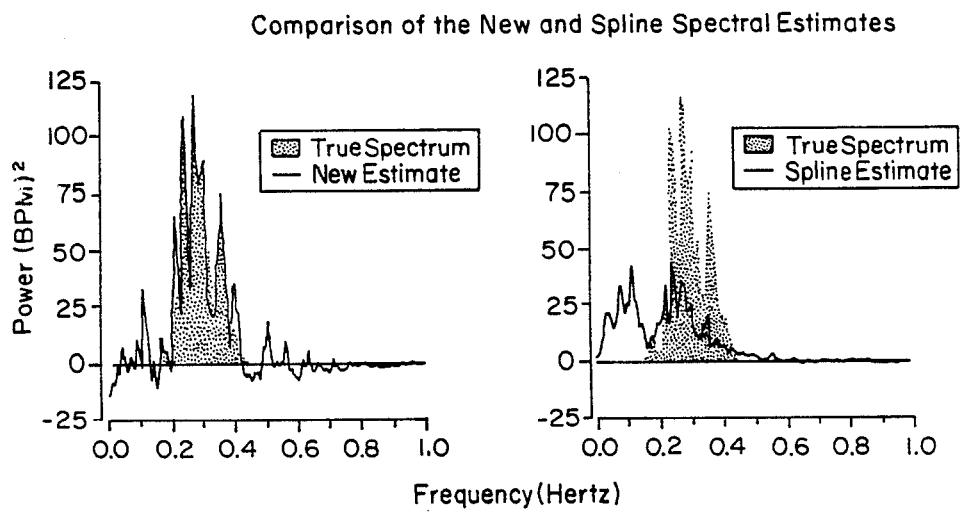
FIG. 2b is a graph comparing the true heart rate spectrum with an estimate computed according to the present invention.
FIG. 2c is a graph comparing the true heart rate spectrum with an estimate computed by the spline technique.

We first computed the true spectrum of the 5 minute HR[n] using all 600 points of HR[n]. We then used the "missing data" pattern for v[n] and computed the spectral estimate $S_{HR}(f)$ described here. The true and estimated (by the method of the invention) spectra are shown in FIG. 2b. This estimated spectrum compares favorably to the true spectrum.

We then computed a spectral estimation derived from a splined version of HR[n]. Splining is a commonly used ad hoc "fix" for obscured data. In the splined version, obscured values of HR[n] were filled in by linear splines joining bordering regions where HR[n] was known. The spectral estimate from splined HR[n] and the true spectrum are shown in FIG. 2c. Note that the splined spectrum not only underestimates the 0.2–0.4 Hz respiratory peak, but also creates substantial ficitious power in the 0–0.2 Hz band.

REFERENCES

[1] S. Akselrod, D. Gordon, F. A. Ubel, D. C. Shannon, A. C. Barger, R. J. Cohen, "Power spectrum analysis of heart rate fluctuations: A quantitative probe of beat-to-beat cardiovascular control," *Scence*, vol. 213, pp. 220–222, 1981.

[2] T. J. van den Akker, A. S. M. Koeleman, L. A. H. Hogenhuis, O. Rompelman, "Heart rate variability and blood pressure oscillations in diabetics with autonomic neuropathy," *Automedica*, pp. 201–208, 1983.

[3] B. Pomerantz, R. J. B. Macaulay, M. A. Caudill, I. Kutz, D. Adam, D. Gordon, K. M. Kilborn, A. C. Barger, R. J. Cohen, H. Benson, "Assessment of autonomic function in humans by heart rate spectral analysis," *Am. J. Physiol.* vol. 248, pp. H 151–153, 1985.

[4] M. Pagani, F. Lombardi, S. Guzzetti, O. Rimoldi, R. Furlan, P. Pizzinelli, G. Sandrone, P. Malfatto, S. Del'Orto, E. Piccaluga, M. Turlel, G. Baselli, S. Cerutti, A. Malliani, "Power spectral analysis of heart rate and arterial pressure variabilities as a marker of sypatho-vagal interaction in man and conscious dog," *Circ. Res.*, vol 59, pp. 178–193, 1986.

[5] G. A. Myers, G. J. Martin, N. M. Magid, P. S. Barnett, J. W. Schadd, J. S. Weiss, M. Lesch, D. H. Singer, "Power spectral analysis of heart rate variability in Sudden Cardiac Death: comparison to other methods," *IEEE Trans. Biomed. Eng.*, vol. BME-33, pp. 1149–1156, 1986.

[6] D. Gordon, V. L. Herrera, L. McAlpine, R. J. Cohen, S. Akserod, P. Lang, W. I. Norwood, "Heart-rate spectral analysis: A nonoinvasive probe of cardiovascular regulation in critically ill children with heart disease," *Pediatric Cardiology*, vol. 9, pp. 69–77, 1988.

[7] J. P. Saul, Y. Arai, R. D. Berger, L. S. Lilly, W. S. Colluci, R. J. Cohen, "Assessment of autonomic regulation in chronic congestive heart failure by heart rate spectral analysis," *Am. J. Cardio.*, vol. 61, pp. 1292–1299, 1988.

[8] P. A. Scheinok, "Spectral analysis with randomly missed observations: the binomial case," *Ann. Math. Statis.*, vol. 36, pp. 971–977, 1965.

[9] P. Bloomfield, "Spectral analysis with randomly missing observations," *J. R. Statis. Soc. B*, pp. 369–380, 1970.

[10] E. Parzen, "On spectral analysis with missing observations and amplitude modulation," *Sankhya A*, vol. 25, pp. 383–392, 1963.

[11] G. M. Jenkins, D. G. Watts, Spectral Analysis and its Applications, Holden-Day, Oakland, California, 1968.

[12] L. Ljung, System Identification: Theory for the User, Prentice-Hall, 1987.

[13] R. D. Berger, S. Akseirod, D. Gordon, R. J. Cohen, "An efficient algorithm for spectral analysis of heart rate variability," *IEEE Trans. Biomed. Eng.*, vol. BME-33, pp. 900–904, 1986.

What is claimed is:

1. Method for characterizing the fluctuations of a signal representing an underlying biological process, said signal being intermittently obscured by a relatively independent process resulting in a corrupted signal comprising:

noting the time intervals during which the obscuring process is occurring, constructing from the intervals a windowing function which makes a transition from one towards zero as the process obscures the signal and a transition towards one as the process terminates, and using the windowing function to weight the relative contributions of corresponding segments of the corrupted signal to create a new signal, whereby a characterization of the statistical properties of the new signal can be made to approximate the characterization of the statistical properties of the signal in the absence of the effect of the obscuring process.

2. The method of claim 1 wherein the weighting comprises computing the product of the windowing function and the corrupted signal to create the new signal, and wherein the fluctuations are characterized by an estimate of the autocorrelation function of the signal in the absence of the effect of the obscuring process comprising:

computing the autocorrelation of the new signal, computing the autocorrelation of the windowing function, and computing the quotient of the autocorrelation function of the new signal and the autocorrelation of the windowing function.

3. The method of claim 2 further comprising computing a power spectrum estimate from the estimate of the autocorrelation function.

4. The method of claims 1, 2, or 3 wherein the signal is heart rate.

5. The method of claims 1, 2, or 3 wherein the obscuring process is atrial or ventricular ectopic beats.

6. The method of claims 1, 2, or 3 wherein the signal is arterial blood pressure.

7. The method of claims 1, 2, or 3 wherein the signal is cardiac output.

8. Method for characterizing the joint fluctuations between a first signal representing a first underlying biological process, said first signal being intermittently obscured by a first process resulting in a first corrupted signal, and a second signal representing a second underlying biological process, said second signal being intermittently obscured by a second process (which may or may not be the same as the first obscuring process) resulting in a second corrupted signal in which each of the first and second signals are relatively independent of each of the first and second obscuring processes comprising:

noting the time intervals during which the first obscuring process is occurring, constructing from the intervals a first windowing function which makes a transition from one towards zero as the first process obscures the first signal and a transition towards one as the first process terminates, noting the time intervals during which the second obscuring process is occurring, constructing from the second set of time intervals a second windowing function which makes a transition from one towards zero as the second process obscures the second signal and a transition towards one as the second process terminates, computing the product of the first corrupted signal with the first windowing function to create a new first signal, computing the product of the second corrupted signal with the second windowing function to create a new second signal, computing the crosscorrelation of the two new signals, computing the crosscorrelation of the two windowing functions, and computing the quotient of the crosscorrelation of the new signals and the crosscorrelation of the windowing functions to produce an estimate of the crosscorrelation function between the two signals in the absence of the effects of the obscuring processes.

9. The method of claim 8 further comprising computing an estimate of the cross-spectrum of the first and second signals in the absence of the effects of the obscuring processes from the estimate of the crosscorrelation function.

10. Method for characterizing the fluctuations between a first signal representing a first underlying biological process, said first signal being intermittently obscured by a first process resulting in a first corrupted signal, and a second signal representing a second underlying biological process, said second signal being intermittently obscured by a second process (which may or may not be the same as first obscuring process) resulting in a second corrupted signal in which each of the first and second signals are relatively independent of each of the first and second obscuring processes comprising:

noting the time intervals during which the first obscuring process is occurring, constructing from the intervals a first windowing function which makes a transition from one towards zero as the first process obscures the first signal and a transition towards one as the first process terminates, computing the product of the first corrupted signal and the first windowing function to create a new first signal, computing the autocorrelation of the new first signal, computing the autocorrelation of the first windowing function, computing the quotient of the autocorrelation of the new first signal and the autocorrelation of the first windowing function to produce an estimate of the autocorrelation function of the first signal in the absence of the effect of the first obscuring process, computing an estimate of the power spectrum of the first signal in the absence of the effect of the first obscuring process from the estimate of the autocorrelation function, noting the time intervals during which the second obscuring process is occurring, constructing from the second set of time intervals a second windowing function which makes a transition from one towards zero as the second process obscures the second signal and a transition towards one as the second process terminates, computing the product of the second corrupted signal with the second windowing function to create a new second signal, computing the crosscorrelation of the two new signals, computing the crosscorrelation of the two windowing functions, computing the quotient of the crosscorrelation of the new signals and the crosscorrelation of the windowing functions to generate an estimate of the crosscorrelation function of the two signals in the absence of the effects of the obscuring processes, computing from the estimate of the crosscorrelation function an estimate of the cross-spectrum of the two signals in the absence of the effects of the obscuring process, and computing the quotient of the estimates of the crossspectrum and the power spectrum to generate an estimate of the transfer function between the two signals in the absence of the effects of the obscuring processes.

11. The method of claim 10 further comprising computing the inverse Fourier transform of the estimate of the transfer function to generate an estimate of the impulse response function between the first and second signals in the absence of the effects of the obscuring processes.

12. Method for characterizing the fluctuations between a first signal representing a first underlying biological process, said first signal being intermittently obscured by a first process resulting in a first corrupted signal, and a second signal representing a second underlying biological process, said second signal being intermittently obscured by a second process (which may or may not be the same as the first obscuring process) resulting in a second corrupted signal in which each of the first and second signals are relatively independent of each of the first and second obscuring processes comprising:

noting the time intervals during which the first obscuring process is occurring, constructing from the intervals a first windowing function which makes a transition from one towards zero as the first process obscures the first signal and a transition towards one as the first process terminates, computing the product of the first corrupted signal and the first windowing function to create a new first signal, computing the autocorrelation of the new first signal, computing the autocorrelation of the first windowing function, computing the quotient of the autocorrelation of the new first signal and the autocorrelation of the first windowing function to produce an estimate of the autocorrelation function of the first signal in the absence of the effects of the obscuring processes, noting the time intervals during which the second obscuring process is occurring, constructing from the second set of time intervals a second windowing function which makes a transition from one towards zero as the second process obscures the second signal and a transition towards one as the second process terminates, computing the product of the second corrupted signal and the second windowing function to create a new second signal, computing the crosscorrelation of the two new signals, computing the crosscorrelation of the two windowing functions, computing the quotient of the crosscorrelation of the new signals and the crosscorrelation of the windowing functions to produce an estimate of the crosscorrelation function of the two signals in the absence of the effects of the obscuring processes, and directly computing an estimate of the impulse response function in the absence of the effects of the obscuring processes from the estimates of the crosscorrelation and the autocorrelation functions.

13. The method of claim 12 further comprising computing the Fourier transform of the estimate of the impulse response function to generate an estimate of the transfer function between the first and second signals in the absence of the effects of the obscuring processes.

14. Method for characterizing the fluctuations between a first signal representing a first underlying biological process, said first signal being intermittently obscured by a first process resulting in a first corrupted signal, and a second signal representing a second underlying biological process, said second signal being intermittently obscured by a second process (which may or may not be the same as the first obscuring process) resulting in a second corrupted signal in which each of the first and second signals are relatively independent of each of the first and second obscuring processes comprising:

noting the time intervals during which the first obscuring process is occurring, constructing from the intervals a first windowing function which makes a transition from one towards zero as the first process obscures the first signal and a transition towards one as the first process terminates, computing the product of the first corrupted signal and the first windowing function to create a new first signal, computing the autocorrelation of the new first signal, computing the autocorrelation of the first windowing function, computing the quotient of the autocorrelation of the new first signal and the autocorrelation of the first windowing function to produce an estimate of the autocorrelation function of the first signal in the absence of the effects of the obscuring processes, noting the time intervals during which the second obscuring process is occuring, constructing from the second set of time intervals a second windowing function which makes a transition from one towards zero as the second process obscures the second signal and a transition towards one as the second process terminates, computing the product of the second corrupted signal with the second windowing function to create a new second signal, computing the crosscorrelation of the two new signals, computing the crosscorrelation of the two windowing functions, computing the quotient of the crosscorrelation of the new signals and the crosscorrelation of the windowing functions to generate an estimate of the crosscorrelation function of the two signals in the absence of the effects of the obscuring processes, computing an estimate of the cross-spectrum of the first and second signals in the absence of the effects of the obscuring processes from the estimate of the crosscorrelation function, and directly computing an estimate of the transfer function of the first and second signals in the absence of the effects of the obscuring processes from the estimates of the crosscorrelation function and the autocorrelation function.

15. The method of any of claims 8–14 wherein one of the signals is heart rate.

16. The method of any of claims 8–14 wherein one of the obscuring processes is atrial or ventricular ectopic beats.

17. The method of any of claim 8–14 wherein one of the signals is aterial blood pressure.

18. The method of any of claims 8–14 wherein one of the signals is cardiac output.

19. Method for characterizing the fluctuations of a signal representing an underlying biological process, said signal being intermittently obscured by a relatively independent process resulting in a corrupted signal comprising:

noting the time intervals during which the obscuring process is occurring, constructing from the time intervals a windowing function which makes a transition from one towards zero as the process obscures the signal and a transition towards one as the process terminates, computing the product of the corrupted signal and the windowing function to create a new signal, computing the autocorrelation of the new signal, computing the autocorrelation of the windowing function, computing the quotient of the autocorrelation of the new signal and the autocorrelation of the windowing function, and computing an estimate of the power spectrum of the signal in the absence of the effect of the obscuring process from the quotient.

* * * * *

UNITED STATES PATENT AND TRADEMARK OFFICE
CERTIFICATE OF CORRECTION

PATENT NO. : 4,979,110

DATED : December 18, 1990

INVENTOR(S) : Paul Albrecht, et al

It is certified that error appears in the above-identified patent and that said Letters Patent is hereby corrected as shown below:

Col. 4 line 22: Replace "$\tilde{n}$" (third occurence) with --n--.
      line 23: Replace "$\tilde{n}$" (third occurence) with --n--.
      line 43: Replace "where $\tilde{x}$" with --where x--.

Column 6, line 29: Replace "$\widetilde{HR}$" with --HR--.
      line 41: Replace "$\widetilde{HR}$" with --HR--.
      line 61: Replace "HR" with --HR--.

Column 7, line 49: Replace "HR" with --$\widetilde{HR}$--.
      line 56: Replace "HR" with --$\widetilde{HR}$--.

Column 8, line 01: Replace "HR" with --$\widetilde{HR}$--.
      line 21: Replace "$S_{HR}(f)$" with --$\hat{S}_{HR}(f)$--.

Signed and Sealed this

First Day of December, 1992

Attest:

DOUGLAS B. COMER

Attesting Officer      Acting Commissioner of Patents and Trademarks